United States Patent [19]

Brånemark

[11] Patent Number: 5,702,443
[45] Date of Patent: Dec. 30, 1997

[54] ANCHORING ELEMENT FOR IMPLANTATION IN TISSUE, FOR HOLDING PROSTHESES, ARTIFICIAL JOINT COMPONENTS OR THE LIKE

[75] Inventor: Per-Ingvar Brånemark, Molndal, Sweden

[73] Assignee: Medevelop AB, Gothenburg, Sweden

[21] Appl. No.: 463,976

[22] Filed: Jun. 5, 1995

Related U.S. Application Data

[62] Division of Ser. No. 233,311, Apr. 26, 1994, abandoned.

[30] Foreign Application Priority Data

Apr. 27, 1993 [SE] Sweden ................... 9301407

[51] Int. Cl.$^6$ ................................ A61F 2/02
[52] U.S. Cl. .................. 623/11; 623/66; 411/387; 411/421
[58] Field of Search ................... 411/421, 420, 411/418, 387, 386; 623/13, 14, 66, 16, 11; 606/60, 65, 66, 72, 73; 433/174, 221, 225

[56] References Cited

U.S. PATENT DOCUMENTS 4,010,671  3/1977  Hubbard ................... 411/418
4,697,969  10/1987  Sparkes ................... 411/387
4,842,467  6/1989  Armstrong ................ 411/399
5,071,301  12/1991  Engelhardt ............... 411/386
5,094,618  3/1992  Sullivan .................. 623/16

FOREIGN PATENT DOCUMENTS 12651  of 1885  United Kingdom ....... 411/418

Primary Examiner—Michael J. Milano
Attorney, Agent, or Firm—Ostrolenk, Faber, Gerb & Soffen, LLP

[57] ABSTRACT

An anchoring element for implantation in bone or other tissue takes the form of an externally threaded screw, for example of titanium or other tissue compatible material. Such an anchoring element may be used, for example for holding prostheses or artificial joint components. To increase its rotational stability and prevent the element from becoming unscrewed, the threads of the screw are provided with notches, for example by forming spiral or straight grooves in the peripheral threaded surface of the element, which grooves intersect the thread turns to form these notches. After such an anchoring element has been implanted in bone tissue for example, the tissue draws into the notches to provide keys preventing rotation and unscrewing of the anchoring element.

9 Claims, 2 Drawing Sheets

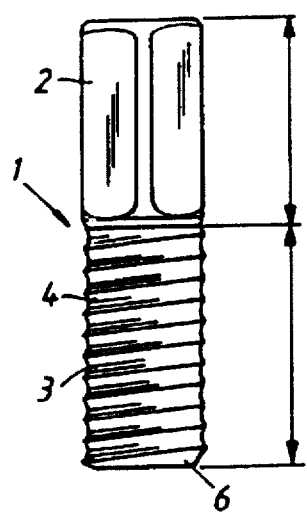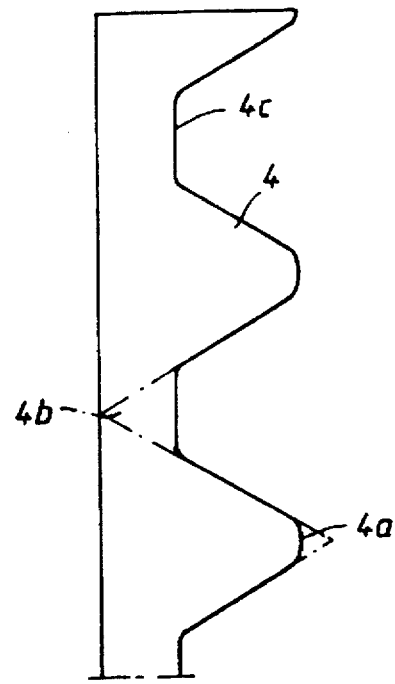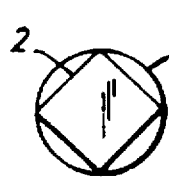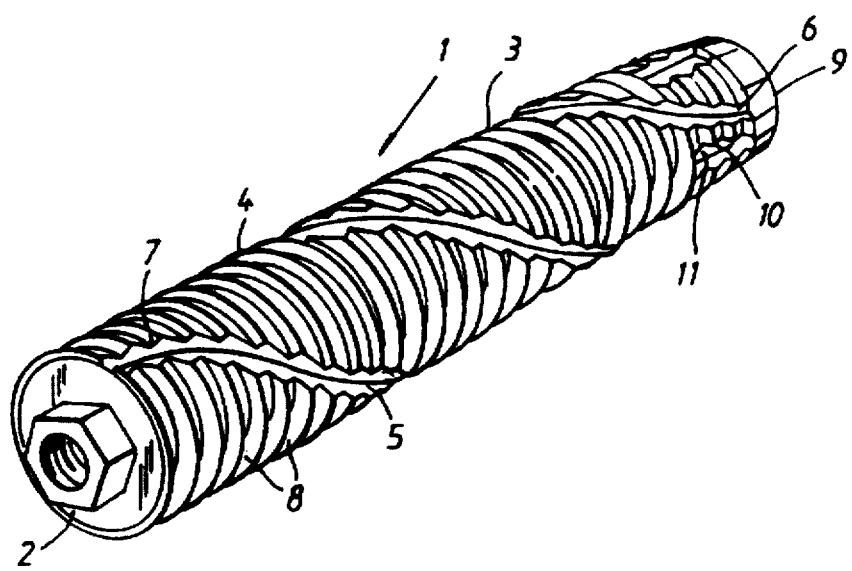

ANCHORING ELEMENT FOR IMPLANTATION IN TISSUE, FOR HOLDING PROSTHESES, ARTIFICIAL JOINT COMPONENTS OR THE LIKE

This is a division of application Ser. No. 08/233,311, filed Apr. 26, 1994, now abandoned.

The present invention relates to an anchoring element for implantation in tissue for holding prostheses, such as amputation prostheses, artificial joint components and the like, the anchoring element being of a tissue compatible material. More particularly, the invention relates to such an anchoring element which is of substantially rotationally symmetric form with external threads arranged on at least part of its peripheral surface and extending towards its insertion end. Such a fixture is herein referred to as being "of the kind specified".

Within the dental field, for instance, implantable anchoring elements of the above kind have been used for many years with great success for anchoring single artificial teeth and for anchoring dental bridges. For example, U.S. Pat. No. 5,064,425 describes such anchoring elements or fixtures intended for application in a bore prepared in the osseous tissue prior to implantation. After screwing the fixture into the bore it is allowed to become attached by growth to the tissue over a substantial period of time (about four months). Thereafter the upper part of the fixture is uncovered for attachment of a tooth or dental bridge by, in most cases, use of appropriate spacers.

Generally, such an anchoring element or fixture consists of a screw-like titanium body provided with external threads, wherein the peripheral surface of the body which contacts the tissue and, thus, also the threads has a particular surface structure for optimal cooperation with surrounding tissue. This specific surface structure comprises a large number of micropits and macropits arranged in the surface for establishment of points of support and attachment for abutting tissue cells and their cell extensions (U.S. Pat. No. 4,330,891 and EP-0338576). In combination with a favourable surgical technique especially developed for this purpose, the required cooperative interaction between the micropitted implant surface and the tissue cells and cell extensions is achieved, resulting in the desired biological anchoring.

A comprehensive clinical follow-up study of such implants has shown that the fixtures have excellent anchoring properties in respect of axial loads.

In connection with more recently proposed uses of such anchoring elements for anchoring of prosthetic components, particularly in respect of various joint designs, such as finger joints, hip joints, hand joints, etc. it has, however, become obvious that attention must also be given to the torsional stability of the fixtures because of the occurrence of non-axial loads. Such rotational stability is necessary to prevent the fixtures from loosening as a result of repeated torsional loading which may cause rotational displacement of such a fixture every time such torsional loading occurs. Even if such a fixture, after such rotational displacement, were to become firmly attached by tissue growth in its new position the anchoring capacity of the fixture in the surrounding tissue would still be impaired.

It is an object of the present invention is to minimise the problems and difficulties described above and to provide an anchoring element of the kind specified which provides substantially increased rotational stability in use than known anchoring elements while preserving the capacity for coping with axial loads, and which anchoring element is thereby less prone to come loose.

In accordance with one aspect of the invention, there is provided an anchoring element of tissue compatible material for implantation in tissue and comprising a body of generally rotationally symmetrical form having a central axis, the anchoring element having an outer peripheral surface provided with a screw thread and wherein a notch is formed across at least one turn of the screw thread whereby tissue may grow into said notch, when the anchoring element is implanted in tissue, to form a key to inhibit rotation of the anchoring element in the tissue.

Preferably the notches have a depth corresponding to that of said external threads.

In a preferred embodiment of the invention the notches are formed by at least one generally spirally extending groove intersecting the screw threads, the pitch of said groove being substantially greater than that of the screw thread. Alternatively, the notches may be formed by a plurality of grooves which extend parallel with the axis of the anchoring element and intersect a plurality of turns of the screw thread.

Where the groove is in the form of a spiral the pitch of the groove is preferably at least three times greater than the pitch of the screw thread.

The notches in adjacent thread turns may be arranged at a distance from each other along an imaginary spiral line.

Two or more spiral grooves may be provided on the peripheral surface of the element. For example a plurality of spiral grooves of the same hand and pitch may be provided, the grooves being spaced apart circumferentially of the element. Each of these grooves may extend over the entire externally threaded surface of the element.

The notches can also be formed by grooves extending generally parallel with the axis of the element. Such grooves preferably extend over at least five adjacent turns of the external thread. Such axial grooves can also be displaced with respect to one another longitudinally of the element.

Preferably, the grooves have a wedge-formed cross section. The thread crests are preferably rounded off and the lands between adjacent thread flanks and which lands define the root diameter of the anchoring screw, are substantially wider, in the axial direction than is usually the case for screws for general engineering purposes.

Preferred embodiments of the invention are described below by way of example with reference to the accompanying drawings.

In the drawings:

FIG. 1 is a side elevation view of a conventional anchoring element;

FIG. 2 is a top view of the element of FIG. 1;

FIG. 3 is a partial view in section through the threads of the element of FIG. 1 showing the thread profile;

FIG. 4 is a perspective view of an anchoring element forming a first embodiment of the invention.

Figure 5:
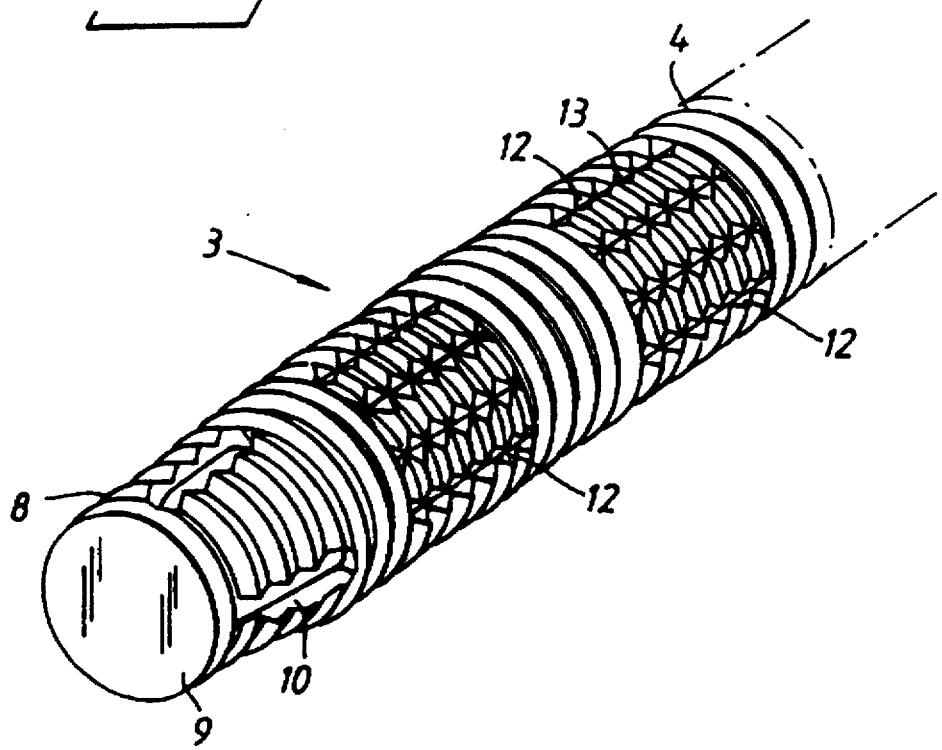
FIG. 5 is a perspective view, showing a portion of an anchoring element forming a second embodiment of the invention.

In the drawings an anchoring element for implantation in tissue for example bone, is indicated at 1.

FIGS. 1 to 3 show a conventional anchoring element. Such an anchoring element 1 is made of a tissue compatible material, such as titanium, and comprises an upper coupling portion 2 for attachment to prosthesis components, artificial joint components, etc., and a lower anchoring portion 3 which along its external peripheral surface is provided with a screw thread 4 extending towards the lower end of the element 1, i.e., the insertion end 6, which is the end of the element which, in use, is inserted first into the bore prepared for the element in the bone or other tissue in which the element is to be implanted. In the embodiment shown here the threads 4 are right-handed. A suitable form for such external threads is shown in FIG. 3. As illustrated, in profile, the thread crests 4a are rounded while lands between thread flanks are flattened. Reference 4b indicates a notional portion of the region between adjacent thread flanks which would result from producing the sloping thread flanks inwardly until they met.

In order to achieve biologically optimal anchoring in tissue, at least those areas of the anchoring element 1 which, in use, contact the tissue have a special surface structure comprising micropits and/or macropits located in close vicinity to each other. In accordance with terminology conventionally used in this area of technology, by the term "micropits" the expert understands depressions in the surface with dimensions of from 10 to 10,000 nm, normally from 10 to 300 nm, and by the term "macropits" depressions in the surface with dimensions of from a few μm to 200 μm and more. Various methods for preparing micropits and macropits, respectively, are known and described in, for instance, U.S. Pat. No. 4,330,891 and EP-0338576.

These micropits are intended to form points of support and attachment for the tissue cells and their cell extensions, respectively, and, in combination with a favourable surgical technique provide the conditions required for the desired biological cooperation between implant surface and surrounding tissue. Comprehensive clinical studies have demonstrated that such surface structure provides superior anchoring between implant surface and surrounding cell tissue. This anchoring technique is also called osseointegration.

Figure 6:
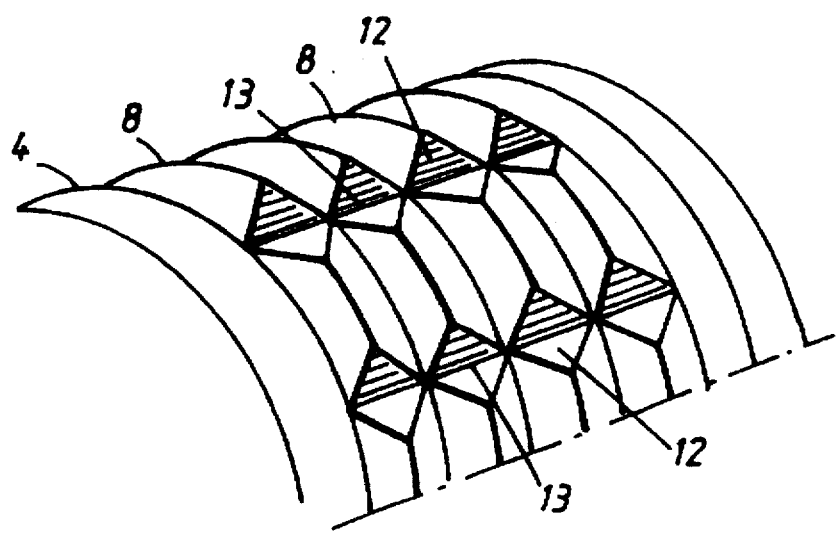
FIG. 6 is an enlargement of part of FIG. 5 showing a detail of the external peripheral surface of the anchoring element.

In FIGS. 4 to 6 are shown two different forms of anchoring element embodying the invention. In each of these forms, the anchoring element takes the form of a body having general rotational symmetry about a central axis. More specifically, the anchoring element in these embodiments is a cylindrical body having an external screw thread 4, which preferably has the same thread form as illustrated in FIG. 3. The anchoring element in each embodiment is preferably of titanium or has an outer layer or coating of titanium for contact with the bone or other tissue in which the element is to be implanted. The embodiment shown in FIG. 4 has a groove 5 extending in a spiral around the element, about its axis, the groove 5 intersecting each of the turns of the thread 4, the groove 5 extending from the upper end 2 of the element 2 towards its lower, insertion end 6. The depth of the spiral groove 5 substantially corresponds to the depth of the thread 4. The groove 5 is preferably wedge-shaped in section transverse to its length, so that the groove is wider at the level of the thread crests than at the level of the thread roots. As is evident from FIG. 4 the spiral-groove 5 has a substantially greater pitch than the thread 4, and thus forms a notch 7 in each turn 8 of the thread 4. The cross sectional shape of each notch 7 thus corresponds with that of groove 5. In order not to affect the screwing insertion of the element into the bore prepared beforehand, the spiral-formed groove should run in the same direction, i.e. should be of the same hand, as the thread 4.

Many variations of the embodiment shown in FIG. 4 are, of course, conceivable within the scope of the invention. Thus the spiral groove 5 can be confined to a section only of the threaded peripheral surface of element 1. In such case, the groove 5 preferably extends over at least five turns of the thread 4. Furthermore, several spiral grooves 5, preferably of the same hand and pitch, can be provided, spaced apart from one another around the circumference of the element 1. Alternatively the threaded surface of the anchoring element may be formed with a plurality of short longitudinal grooves, each providing a notch through only one thread turn or each providing notches through only a few thread turns. In this case the individual short grooves, or the individual notches formed thereby, may lie on an imaginary spiral line over the peripheral surface of the anchoring element.

The anchoring element shown in FIG. 4 is self-tapping; by way of example it may for instance have the general form described in U.S. Pat. No. 5,064,425. That is to say it may have a closed bottom 9 and a number of axially extending slits 10 arranged just above said closed bottom, said slits cooperating with cavities 11 present in the element 1 for collection of "tissue cuttings" when screwing the anchoring element 1 into a bore prepared in the tissue beforehand. In this connection the slits 10 provide suitable cutting edges.

FIGS. 5 and 6 show an alternative arrangement of notches 7 across the screw thread for increasing rotational stability in accordance with the invention. In this embodiment, instead of spirally extending groove 5 shown in FIG. 4, there are provided in the periphery of the anchoring element, grooves 13 which extend parallel with the axis of the element, the grooves 13 intersecting the thread turns in respective notches. The grooves 13, like the groove 7 may be wedge-shaped in cross-section. Again, the grooves are preferably at the same depth as the thread 4, and they can be arranged in close proximity to each other or at a greater distance from each other. These grooves 13 can also be displaced longitudinally with respect to each other and are preferably of such length as to form notches 12 in a number of adjacent turns 8 of the thread 4 located adjacent to each other, preferably in at least three adjacent turns 8.

As shown in FIG. 5 such axial grooves 13 are preferably arranged in each of several axially spaced zones or sections along the threaded surface of the anchoring element 4. In such a case they should primarily be arranged at least in the sections of anchoring element 1 intended to have load-bearing contact with the surround osseous tissue. From FIG. 6 is evident how these axial grooves 13 provide notches 12 in the turns of the thread 3.

Experiments have shown that the anchoring element proposed in accordance with the invention and provided with rotationally stabilizing notches provides for a substantial increase of rotational stability compared with prior known anchoring elements. Once the anchoring element has been implanted, the surrounding tissue will grow into these notches, and will effectively form "keys" in these notches, preventing the anchoring element from moving under torsional loads and thus becoming unscrewed, in effect. However, it has also been observed that the rotationally stabilizing notches proposed by the invention do not adversely affect the function of the external thread 4 in allowing the anchoring element to be screwed into the bore provided in the bone or other tissue during implantation nor do these notches adversely affect the axial load stability provided by the external thread.

It will, of course, be appreciated that the provision of a groove extending along the external thread in the form of a spiral is not confined to the particular anchoring elements shown in FIGS. 4 and 5 and which have features disclosed in U.S. Pat. No. 5,064,425. Thus, the groove shown in FIG. 4 and also the axially extending grooves shown in FIG. 5 can, of course, be used with anchoring elements lacking a closed bottom and self-threading properties.

The invention is, of course, not limited to the embodiments described above with reference to the drawings but can be varied in many ways within the scope of the appended claims. Thus the dimensions of the external threads 4, in general, can coincide with the prior known design shown in FIG. 3. Furthermore such anchoring elements also can be used for fixtures penetrating the skin and for other purposes, such as, for instance, electrical wires. An anchoring element proposed embodying the invention can be also used for holding hip joints and such an anchoring element should, of course, be of such a length as to allow safe anchorage within the bone. In respect of hip prostheses, in particular, there exists a great need for rotationally stabilized fixtures, since substantial problems are inherent in known anchoring devices. Known anchoring devices very often tend to loosen after a relatively short period of use.

I claim:

1. An anchoring element formed of a tissue compatible material for extended prosthetic implantation in tissue comprising:

a body of a generally rotationally symmetrical form having a central axis, the anchoring element having an outer peripheral surface provided with a screw thread having a thread crest, the thread crest being rounded in profile, and wherein a notch is formed across at least one turn of the screw thread for tissue growth into the notch when the anchoring element is implanted in the tissue, said notch dividing the thread into thread sections having lengths, the notch forming a key to inhibit rotation of the anchoring element in the tissue, the notch extending parallel with the axis of the anchoring element, and the width of the notch in the direction of the thread being substantially smaller than the length of each thread section.

2. An anchoring element according to claim 1, comprising a plurality of notches formed by a plurality of portions of a groove extending along the outer peripheral surface of the anchoring element and intersecting a plurality of the turns of the screw thread.

3. An anchoring element according to claim 2, wherein the groove extends across at least five turns of the thread.

4. An anchoring element according to claim 1, in which the notch has a depth corresponding to that of the thread.

5. An anchoring element according to claim 1, in which several groups of notches are formed in the thread, the notches of each group being formed by portions of a respective groove extending along the outer peripheral surface of the anchoring element and intersecting a plurality of turns of the thread, the grooves being spaced apart circumferentially of the anchoring element.

6. An anchoring element according to claim 1, wherein each the notch is of wedge-shaped cross-section, being wider, in the circumferential direction of the anchoring element, at the crest of the respective thread turn than at the thread root.

7. An anchoring element according to claim 1, wherein the thread crests are rounded in profile.

8. An anchoring element according to claim 1, which is made of titanium.

9. An anchoring element according to claim 1, which has a surface coating or layer of titanium providing the external peripheral surface of the anchoring element.

* * * * *